United States Patent [19]

Klein

[11] 4,388,301

[45] Jun. 14, 1983

[54] METHOD AND COMPOSITION FOR TREATING ACNE

[75] Inventor: Robert W. Klein, North Wales, Pa.

[73] Assignee: William H. Rorer, Inc., Fort Washington, Pa.

[21] Appl. No.: 373,442

[22] Filed: Apr. 30, 1982

Related U.S. Application Data

[63] Continuation-in-part of Ser. No. 270,928, Jun. 12, 1981, abandoned, which is a continuation-in-part of Ser. No. 139,401, Apr. 11, 1980, abandoned, which is a continuation of Ser. No. 967,485, Dec. 7, 1978, abandoned.

[51] Int. Cl.³ .................... A61K 33/06; A61K 33/08
[52] U.S. Cl. .................................. 424/154; 424/160; 424/163; 424/357
[58] Field of Search ............... 424/160, 163, 357, 154

[56] References Cited

U.S. PATENT DOCUMENTS 1,800,502  4/1931  Brown ........................... 424/160 X
2,156,790  5/1939  Missbach ....................... 424/160 X

OTHER PUBLICATIONS

Handbook of Non-Prescription Drugs, 5th ed., pp. 317-323, (1977).
Kirk-Othmer-Encyclopedia of Chemical Technology, vol. 5, 1964, pp. 554, 580 & 581.

*Primary Examiner*—Leonard Schenkman
*Attorney, Agent, or Firm*—James A. Nicholson; Austin R. Miller; John Lezdey

[57] ABSTRACT

A method of treating skin conditions utilizing a deodorized composition containing soluble polysulfide compounds and the composition therefor.

18 Claims, No Drawings

4,388,301

METHOD AND COMPOSITION FOR TREATING ACNE

This is a continuation-in-part of Ser. No. 270,928 filed June 12, 1981 which is a continuation-in-part of Ser. No. 139,401 filed Apr. 11, 1980 which is a continuation of Ser. No. 967,485, filed Dec. 7, 1978, all now abandoned.

FIELD OF THE INVENTION

This invention relates to methods of topically treating acne and oily skin and compositions useful for said treatment. The invention also relates to a method for deodorizing compositions containing polysulfide compounds or sulfurated lime solutions which contain such compounds that are intended for topical administration, and for preventing staining of skin or fabric as well as discoloration of jewelry by the use of such compounds.

BACKGROUND OF THE INVENTION

It is well established that acne is associated with sebum production and that androgens stimulate sebum production whereas estrogens suppress sebum production; estrogen therapy being indicated as a possible means of treating acne. Several reports indicate that oral contraceptives or the individual active estrogenic components thereof, for example, ethinyl estradiol and derivatives are useful in treating acne in both males and females. In recent years it has become apparent that estrogenic products currently in use possess certain undesirable side effects which must be set against the undoubted benefits resulting from their use. The use of estrogens for the treatment of acne in women can lead to uterine bleeding and spotting and breast tenderness. In men, estrogen administration can have a feminizing effect and may result in gynecomastia and impotence. [IF. Goodman and A. Gilman, *The Pharmacological Basis of Therapeutics*, 4th Ed., The MacMillan Company, p. 1537 (1970)]. Estrogenic therapy has been reported to give rise to other deleterious side effects. For example, diethylstilbestrol, a once widely used and well established estrogen has been implicated as possibly being responsible for vaginal cancer and adenosis in the female offspring of pregnant women treated with the compound (*Lancet*, 1975, 1960). Also, ethinyl estradiol and mestranol, which represent estrogenic compounds in current oral contraceptives, are now known to be involved in certain serious side effects associated with oral contraceptives including depression [*Nature* 243, 58 (1973)], hypertension [*Am. J. Obstet. Gynecol.* 112, 912, (1972)], carbohydrate and lipid abnormalities (*Lancet*, 1969, p. 783), interference with blood clotting mechanism resulting in thrombosis and stroke [Ann. Intern. Med. 72, 111, (1970)], and jaundice [*Am. J. Obstet. Gynecol.* 119, 1965, (1974)]. Consequently, there is a need for an improved method of treating acne.

The present invention provides a novel method and composition of topically treating acne and oily skin with nonsteroidal agents particularly those comprising polysulfide compounds. Polysulfide compounds, particularly those found in a sulfurated lime solution have been found to be effective in the treatment of various skin conditions. However, polysulfide compounds, especially those found in a sulfurated lime solution, which is an amber, staining liquid, yield an objectionable odor which precludes its use on the face or chest. The present invention now provides a means for deodorizing the compositions which contain these polysulfide compounds so as to be generally acceptable for cosmetic and therapeutic use.

SUMMARY OF THE INVENTION

The present invention relates to a method of treating acne and oily skin by the administration of compositions containing polysulfide compounds in a vehicle containing a mixture of clays, and, if desired, pigment extenders.

This invention also relates to pharmaceutical preparations suitable for topically treating acne and oily skin. Thus, in addition to relating to a method of treating acne and oily skin, this invention also relates to anti-acne and anti-seborrheic pharmaceutical preparations.

Additionally, this invention relates to a means for removing any objectionable odor from cosmetic and therapeutic compositions which contain polysulfide compounds for example, sulfurated lime solution, while simultaneously releasing any added perfume fragrances and still retaining its efficacy.

This invention further relates to a method for topically administering a solution of sulfurated lime which is free from objectionable odors.

Still further, the composition of this invention permits the use of sulfurated lime solution without the problem of staining clothing or tarnishing jewelry.

DETAILED DESCRIPTION OF THE INVENTION

As used herein, the term "acne" is intended to mean any inflammatory disease or condition of the sebaceous gland commonly occurring at puberty resulting in comedones, pustules, papules, inflamed nodules or infected cysts. A solution of polysulfide compounds, especially sulfurated lime, in combination with a finely divided sorbent powder consisting of a mixture of clays, namely, a montmorillonite clay together with attapulgite, has been found to be effective in reducing the amount of sebum produced by sebaceous glands.

The compositions of the present invention, when administered to a patient having an acne condition and/or oily skin condition, represents a novel method of treating patient which offers distinct advantages over previously employed methods of treatment, for example, estrogen therapy, in that the compounds employed do not result in certain deleterious side effects resulting with estrogen therapy as will become more apparent hereinafter.

The term "polysulfide compound" as used herein refers to any inorganic di- or polysulfide compound which is pharmaceutically acceptable. Preferable are the water or water-alcohol soluble compounds, although those forming a suspension can also be utilized. The alkali and alkaline earth polysulfide compounds are most preferable since they can form more elegant commercially acceptable compositions with the clay vehicles of this invention.

The alkali metals form polysulfides of general formula $M_2S_n$ containing unbranched $[S_n]^{2-}$ anions. The polysulphides are most conveniently prepared by reaction of the elements in liquid ammonia or by reaction of $M_2S$ with sulphur; the highest polysulfides (with maximum value of n) are prepared by melting $M_2S_{n-1}$ with sulfur. The following polysulfides of the alkali metals are well-established compounds: $Li_2S_2$, $Na_2S_2$, $Na_2S_4$, $Na_2S_5$; $K_2S_2$, $K_2S_3$, $K_2S_4$, $K_2S_5$, $K_2S_6$; $Rb_2S_2$, $Rb_2S_3$, $Rb_2S_5$; $Cs_2S_2$, $Cs_2S_3$, $Cs_2S_5$, $Cs_6S_6$. Preparations of composition $Na_2S_3$, $Rb_2S_4$, $Rb_2S_6$, $Cs_2S_4$ are usually found to be mixtures. In addition to the compounds mentioned, several solvated polysulfides of the alkali metals are known.

The crystal structures of $Na_2S_2$ (two forms) and $K_2S_2$ have been determined. The structures are built from $M^+$ ions and $S^{2-}$ ions; the S—S distance is about 2.15Å. The S—S distance in the $S^{2-}$ ions in disulfides $MS_2$ of transition metals with a pyrite-type or related structure also lie in the range of 2.07–2.21Å; they are significantly longer than the S—S distance (2.04 Å) in elemental sulphur and other covalent compounds containing S—S groups. S—S distances of 2.03–2.04 Å have also been found in the $S_2$ groups in $VS_4$. This may be ascribed to the increase in covalency of the M—S bond with increasing oxidation number of the metal. In several compounds $S^{2-}$ ions coexist with isolated $S^{2-}$ ions.

Crystalline strontium polysulfides $SrS_2$ and $SrS_3$ (two forms) have been prepared by heating of the amorphous products, $CaS_2$, $BaS_2$ and $BaS_3$ have also been prepared. Strontium and barium tetrasulfides are known as hydrates.

While it is known that polysulfides occur naturally within the human body, the pharmacodynamics of sulfur-derived compounds is still not completely understood. To therapeutically interact, transformation of sulfur into an absorbable state is necessary. Volatile, absorbable sulfur in the form of sulfurated lime solution (Vleminckx) has been reported to excel in use over common precipitated sulfur in several dermatologic conditions including acne, seborrheic dermatitis and (early stage) furuncles.

Vleminckx's solution provides both immediate and total availability of soluble drug, differentiating it entirely from elemental particulate sulfur. Of possible significance is the fact that, like peroxides, polysulfides are oxidizing agents.

"Sulfurated lime" as used herein is commercially available and may be prepared according to the procedure disclosed in *Mellor*, Vol. III, p. 740 (1928) and in the U.S. Pharmacopedia XX. Generally, sulfurated lime contains calcium sulfides and polysulfides and the balance being calcium sulfate, thiosulfate and carbonate, and the "ash" from the carbonaceous material from which it is formed.

It has been surprisingly discovered that the combination of a montmorillonite clay and attapulgite removes the odor of the polysulfide solutions, especially sulfurated lime solution, while releasing any perfume odor which may be present in the composition.

The clay which may be utilized in the composition of the present invention are the natural and synthetic montmorillonite clays such as the bentonites, kaolin, hectorite, hectorite-like, smectite, smectite-like, saponite, saponite-like or mixtures thereof in combination with attapulgite.

Montmorillonite is the name of a group of clays with an expanding lattice which are members of the clay-mineral group. The montmorillonites contain aluminum silicates with some montmorillonites having some of the aluminum replaced by magnesium.

The structure of 2:1 layer-lattice clay minerals is well known. Such minerals contain a central layer of cations octahedrally coordinated to oxygen and hydroxyl anions which are linked through shared oxygen anions to two layers of cations tetrahedrally coordinated to oxygen and hydroxyl anions, one on each side of the central octahedral layer. For each unit cell of such clays there are 6 octahedral cation sites and 8 tetrahedral cation sites. The sum of the cationic charges for electroneutrality of the layer-lattices is 12 for the octahedral cation sites and 32 for the tetrahedral cation sites. Thus the 6 octahedral cation sites can be filled with 6 divalent (+2) cations which satisfies the required layer charge. Clays which contain approximately 6 octahedrally coordinated cations are called trioctahedral. The theoretical formula without considering lattice substitutions for trioctahedral 2:1 layer-lattice clay minerals is $(R_6{}^{+2})^{VI}(D^{+4})_8{}^{IV}O_{20}(OH)_4nH_2O$ (interlayer water). The number of cations in the octahedral layer of naturally occurring trioctahedral 2:1 layer-lattice clay minerals is within the range from 5.76 to 6.00. However, the 6 octahedral cation sites can also be filled with 4 trivalent (+3) cations which satisfies the required layer charge. Such clays which contain approximately 4 octahedrally coordinated cations are called dioctahedral. The theoretical formula without considering lattice substitutions for dioctahedral 2:1 layer-lattice clay minerals is:

$[(R^{+3})_4{}^{VI}(D^{+4})_8{}^{IV}O_{20}(OH)_4]nH_2O$ (interlayer water). The number of cations in the octahedral layer of naturally occurring dioctahedral 2:1 layer-lattice clay minerals is within the range from 4.00 to 4.44.

The octahedrally coordinated cation sites can accommodate cations which have an ionic radius not greater than 0.75 Å and the tetrahedrally coordinated cation sites can accommodate cations which have an ionic radius not greater than 0.64 Å. Thus various cations can isomorphously substitute for the divalent cations in the central octahedral layer of trioctahedral clays, for the trivalent cations in the central octahedral layer of dioctahedral minerals, and for the tetravalent cations in the outer tetrahedral layers of both types of minerals. Such substitutions give rise to a charge imbalance within the octahedral and tetrahedral layers in which the substitution occurs. The charge imbalance usually results from the substitution of cations with a smaller cation charge thus creating a negatively charged layer-lattice. This negative charge is neutralized by cations on the surface of the layer lattices.

Naturally occurring hectorite is a trioctahedral 2:1 layer-lattice magnesium silicate smectite clay mineral in which approximately 0.66 $Mg^{2+}$ and approximately 1 $F.^-$ ion per unit cell substitute for $OH^-$. Thus the idealized structural formula for natural hectorite is:

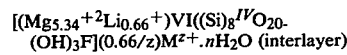

where the $Mg^+$ and $Li^+$ are present in the central octahedral layer and M is the charge balancing cation external to the layer-lattices of valence z. Hectorite-type minerals can be synthesized in which the number of $Li^+$ per unit cell can be varied up to about 1.0 and in which $F^-$ can be substituted for $OH^-$. Thus hectorite-type minerals have the following idealized structural formula:

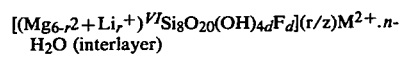

where $O=r=1$ and $O=d=4$. The formula is "idealized" since minor amounts or trivalent cations can substitute in both the octahedral layer and tetrahedral layers and other divalent cations can substitute for Mg. Natural hectorite is also impure and contains such contaminants as calcite, dolomite and other minerals.

The polysulfide compositions of the present invention can be administered in various manners to achieve the desired effect. The amount of polysulfide compounds in the composition will vary with the severity of the acne or oily skin condition, the specific polysulfide utilized and the mode of administration. Generally, the polysulfide compound comprises about 1–20% by weight of the total composition, preferably 2–10% by weight of the total composition. The sorbent powder to be an effective deodorant for the polysulfide compounds must comprise at least about 10–70% by weight of a montmorillonite clay based on the weight of the total composition and 2–30% by weight of attapulgite based on the weight of the total composition.

The sulfurated lime compositions of the present invention have been found to be especially advantageous in the reduction of comedones during the first two weeks of treatment. It is believed that the combination of polysulfide compounds together with other sulfur-containing compounds which are present in sulfurated lime solutions provide increased efficacy when utilized in combination with the clays of the present invention. The absorbing and adsorbing action on the facial oils and the simultaneous desorbing of the sulfurated lime results in an improved response by the patient together with a lowering of irritation.

The topical formulation of the present invention may contain pharmaceutically acceptable surfactants, particularly those having a detergent action to aid in the microabrasion of the uppermost layer of the skin, i.e., horny layer, to provide a smooth feeling to the skin; soothing agents such as camphor; cooling agents such as menthol; dispersing agents, penetrants, perfumes, and a conservation agent such as butylated hydroxytoluene.

The addition of calcium carbonate to the composition has been found to be advantageous for maintaining the composition's alkalinity and color. Also, it is useful in providing a microabrasive effect so as to remove the horny layer of the skin and leave a smooth feeling.

Talc may be added to the composition to improve the slip qualities of the composition on the skin.

A lower alkanol may be added in an amount of 1–10% by weight of the total compositions to yield a smoother mixture and to solubilize facial oils.

An effective amount of the other acne-treating agents or antibiotic agents may be incorporated in the composition such as in an amount of up to about 1–6% by weight of the composition. These additional active ingredients include benzoyl peroxide, salicylic acid, Lincomycin compounds, resorcinol and its derivatives, retinoic acid and its derivatives, tetracycline compounds, sulfur, erythromycin compounds, and the like.

Aerosol preparations containing the polysulfide compounds, in particular, a sulfurated lime solution and the mixture of clays together with extenders in the form of a finely ground powder may also be employed for topical administration. The aerosols may be packaged in a pressurized aerosol container together with a gaseous or liquified propellant, for example, dichlorodifluoromethane, dichlorodifluorethane, carbon dioxide, nitrogen, or propane with the usual adjuvant such as a suspending agent and wetting agents as may be necessary or desirable. Although the present formulation may be applied directly to the site requiring treatment, it is preferably applied in the form of a face mask so that during its application, the absorbing and adsorbing action of the sorbent powder on the face oils takes place and the polysulfides present become more effective in the desired treatment of the skin condition.

The following Examples are illustrative of formulations of compositions according to this invention.

EXAMPLE I

A composition for use as a face mask containing the following composition:

Sulfurated lime solution (Vleminckx's solution)—125 ml
Colloidal aluminum magnesium silicate (VEEGUM) (a montmorillonite type clay)—750 mg
Attapulgite—250 mg
Sodium lauryl sulfate—150 mg
Butylated hydroxytoluene—15 mg
Ethanol—100 ml
Purified water—110 ml was prepared as follows:

Into a beaker containing 125 ml of sulfurated lime solution, 150 mg of sodium lauryl sulfate, 15 mg of butylated hydroxytoluene, 100 ml of ethanol, and 10 ml of purified water was stirred in 750 mg of colloidal aluminum magnesium silicate and 250 mg of attapulgite until a uniform paste was formed. The composition had essentially no sulfur odor and was suitable for forming a face mask useful for treatment of acne.

EXAMPLE II

A composition for the treatment of acne and seborrheic conditions having the following:

Sulfurated lime solution—20 ml
Hectorite clay—40 g
Attapulgite—10 g
Polyethylene glycol monostearate—5 g
Ethanol—5 ml
Purified water—20 ml was prepared as follows:

Into a beaker containing 20 ml of sulfurated lime solution was added 40 g of LAPONITE, a commercially available hectorite clay, and 10 g of attapulgite. 20 ml of purified water and 5 ml of ethanol was then heated and mixed with polyethylene glycol monostearate until uniform. The mixture was then cooled to room temperature and mixed until a thick paste was formed that was spreadable by use of an applicator stick.

EXAMPLE III

A paste for a face mask for use in the treatment of severe acne and having an anti-seborrheic effect comprising:

| | |
|---|---|
| Calcium polysulfide | 10 g |
| Retinoic acid | 12 mg |
| Sodium lauryl sulfate | 5.5 g |
| Bentonite | 40 g |
| Attapulgite | 5 g |
| Alcohol SD | 5.5 ml |
| Purified water | q.s. |
| | 100 | was prepared as follows:

Into a beaker containing 10 g of calcium polysulfide, 110 ml of water and 5.5 ml of a lower alcohol was added with stirring 5.5 g of sodium lauryl sulfate, 12 mg of retinoic acid, 5 g of attapulgite and 40 g of pulverized bentonite clay until a paste of a desired consistency was obtained. The resulting paste may then be applied directly to the site requiring treatment. A current of warm air may then be blown on the face until the mixture dries. The composition is maintained on the face for about 20 to about 30 minutes and then removed by washing with water. The treatment is administered either every other day or daily until the condition treated is alleviated.

If desired, benzoyl peroxide or an antibiotic compound such as erythromycin or tetracycline compounds or derivatives may be added to this formulation in an amount of about 1-6% by weight of the total composition.

Following the procedure of Example III other formulations may be prepared by replacing calcium polysulfide with any other soluble polysulfide compound or mixtures thereof.

EXAMPLE IV

| Ingredients | Percent |
| --- | --- |
| Vleminckx's solution | 6.00 |
| Decyl oleate | 0.60 |
| Alcohol | 7.00 |
| Titanium Dioxide | 3.00 |
| Kaolin | 15.00 |
| Calcium Carbonate | 2.30 |
| Attapulgite | 3.50 |
| Calcium silicate | 2.00 |
| Silica | 0.225 |
| EDTA | 0.10 |
| Paraben | 0.20 |
| Dioctyl sodium sulfosuccinate | 0.16 |
| Fragrance | 0.10 |
| Fatty alkanolamide | 5.00 |
| Partially acetylate polyoxyethylene lanolin ether (Laneth-10 acetate) | 2.00 |
| Sodium sulfate of an ethoxylated fatty alcohol | 5.00 |
| Purified water | q.s. |

The formulation was effective for the treatment of acne and oily skin conditions. Removal of the paste by water washing gave a smooth feeling to the skin.

In the present formulation, replacement of the sulfurated lime solution with a non-soluble polysulfide compound requires extensive stirring (about 3 hours) in order to achieve a uniform mixture with good spreadability.

COMPARATIVE EXPERIMENT A

A sulfur-containing lotion was prepared utilizing a conventional formulation with the following ingredients:

| Ingredients | Percent |
| --- | --- |
| Sulfur (U.S.P.) | 6.00 |
| Cellulose gum | 0.45 |
| Propylene glycol | 3.00 |
| Attapulgite | 2.00 |
| Iron oxide | 1.20 |
| Alcohol | 20.00 |
| Fragrance | 0.10 |
| Fatty alkanolamide | 2.00 |
| Methyl paraben | 0.15 |
| Talc | 7.00 |
| Zinc oxide | 7.00 |
| Deionized water | q.s. |
| Titanium Dioxide | 4.00 |

COMPARATIVE EXPERIMENT B

A lotion was prepared utilizing the formula of Experiment A except that a sulfurated lime solution (Vleminckx's solution) was utilized in lieu of sulfur.

TABLE I

| Sample | Odor | Cosmetic Effect |
| --- | --- | --- |
| 1. Vleminckx's solution | Objectionable | Poor (not suitable for use) |
| 2. Elemental sulfur | Slightly pungent | Poor (could be used) |
| 3. Paste of Experiment IV | Pleasant | Good |
| 4. Lotion of Experiment A | Pleasant | Good |
| 5. Lotion of Experiment B | Slightly Objectionable | Fair (not suitable for use) |

It was noted that elemental sulfur by itself or in a conventional carrier could be utilized by patients without any objectionable odor being present. Use of a sulfurated lime solution by itself or in a conventional carrier such as those containing elemental sulfur still produced an objectionable odor which would prevent use on the face area. A formulation prepared according to Example IV had a pleasant odor and could be utilized for skin care.

EXPERIMENT C

A. Mixtures comprised of 6% sulfurated lime solution and the following clays were prepared with sufficient water to give paste-like consistencies:

TABLE I

| Clay | Test A (parts by wt.) | Odor | Test B (parts by wt.) | Odor |
| --- | --- | --- | --- | --- |
| 1. Bentonite | 10 | Pungent | 20 | Pungent |
| 2. Kaolin | 10 | Pungent | 20 | Pungent |
| 3. Attapulgite | 10 | Pungent | 20 | Pungent |
| 4. Calcium silicate | 10 | Pungent | 20 | Pungent |

The pungent "rotten egg" odor of the sulfurated lime solution was evident although somewhat diminished in each of the formulations. Each mixture caused a light yellow stain when applied to fabric. Contact with silver jewelry resulted in tarnishing.

B. Mixtures were prepared according to the procedure of Part A.

TABLE II

| Clay | Test A (parts by wt.) | Odor | Test B (parts by wt.) | Odor |
| --- | --- | --- | --- | --- |
| 1. Bentonite | 10 | Slight | 20 | Slight |
| Kaolin | 10 | Pungent | 10 | Pungent |
| 2. Bentonite | 10 | None | 20 | None |
| Attapulgite | 10 | | 10 | |
| 3. Bentonite | 10 | Slight | 20 | Slight |
| Calcium Silicate | 10 | Pungent | 10 | Pungent |
| 4. Kaolin | 10 | None | 20 | None |
| Attapulgite | 10 | | 10 | |
| 5. Kaolin | 10 | Slight | 20 | Slight |
| Calcium Silicate | 10 | Pungent | 10 | Pungent |
| 6. Calcium Silicate | 10 | Slight | 20 | Slight |
| Attapulgite | 10 | Pungent | 10 | Pungent |

TABLE III

| Clay | Parts by wt. | Odor |
| --- | --- | --- |
| 1. Bentonite | 9.0 | Slight |
| Attapulgite | 0.5 | Pungent |
| 2. Bentonite | 9.0 | None |
| Attapulgite | 1.5 | |
| 3. Kaolin | 9.0 | Slight |
| Attapulgite | 0.5 | Pungent |
| 4. Kaolin | 9.0 | None |
| Attapulgite | 1.5 | |

The use of 1.5 parts of attapulgite yielded a mixture which was virtually free of sulfurated lime solution odor. Mixtures (2) and (4) caused no staining of fabrics. Contact with silver, gold and chrome plated jewelry caused no tarnishing, even after 10 hours of contact.

EXAMPLE V

| Ingredients | Percent |
| --- | --- |
| Vlem-Dome* | 10.00 |
| Decyl oleate | 0.60 |
| Alcohol | 7.00 |
| Titanium Dioxide | 3.00 |
| Kaolin | 15.00 |
| Calcium Carbonate | 2.30 |
| Attapulgite | 3.50 |
| Calcium silicate | 2.00 |
| Silica | 0.225 |
| EDTA | 0.10 |
| Paraben | 0.20 |
| Dioctyl sodium sulfosuccinate | 0.16 |
| Fragrance | 0.10 |
| Fatty alkanolamide | 5.00 |
| Partially acetylate polyoxyethylene lanolin ether (Laneth-10 acetate) | 2.00 |
| Sodium sulfate of an ethoxylated fatty alcohol | 5.0 |
| Purified water | q.s |

*Vlem-Dome is a tradename of a stabilized mixture of calcium polysulfide, calcium thiosulfate and sulfur of Dome Chemicals, Inc., a Division of Miles Laboratories, Inc.

The formulation is effective for the treatment of acne vulgaris, acne conglobata and deep cystic acne.

I claim:

1. A method for treating acne and oily skin in a patient in need thereof which comprises topically administering to said patient an effective amount of a composition comprising about 1-20% by weight of total composition of an inorganic polysulfide compound in a carrier comprising a sorbent powder, said polysulfide comprising a sulfurated lime solution an inorganic metallic di- or polysulfide compound of the formula $M_2S_n$ containing unbranched $[S_n]^{2-}$ ions, where M designates a metal and n is any number from 2 to the maximum value of n, which polysulfide upon topical administration itself has an objectionable odor, said powder comprising about 10-70% by weight of at least one montmorillonite clay based on the weight of the total composition and about 2-30% by weight of attapulgite based on the weight of the total composition, said powder being present in an amount to deodorize said composition, to absorb and adsorb the skin oils and to release an effective amount of said polysulfide compound to treat said patient.

2. The method of claim 1, wherein said polysulfide compound is a sulfurated lime solution.

3. The method of claim 1, wherein said polysulfide compound is selected from the group consisting of alkali metal and alkaline earth metal polysulfides.

4. The method according to claim 1, including a pharmaceutically acceptable surfactant and a lower alkanol.

5. The method of claim 1, wherein said montmorillonite clay is selected from the group consisting of bentonite, hectorite, smectite, kaolin and saponite.

6. The method of claim 1, including at least one filler selected from the group consisting of talc and calcium carbonate.

7. The method of claim 1, including an effective amount of a compound selected from the group consisting of benzoyl peroxide, retinoic acid, erythromycin, salicylic acid or resorcinol.

8. The method according to claim 1, wherein said polysulfide is calcium polysulfide.

9. A method of treating oily skin in a patient in need thereof which comprises topically administering to said patient an effective amount of a composition comprising 2-10% by weight of a sulfurated lime solution and finely divided powder containing montmorillonite clay powder in an amount of about 10-70% by weight based on the weight of the total composition and about 2-30% by weight of attapulgite based on the weight of the total composition, whereby said clays are present in an amount sufficient to deodorize said composition, to absorb and adsorb skin oils and to release an effective amount of sulfurated lime solution to treat said patient.

10. An anti-acne and anti-seborrheic pharmaceutical composition for topical administration comprising about 1-20% by weight of total composition of an inorganic polysulfide compound in a carrier comprising a sorbent powder, said polysulfide comprising a sulfurated lime solution an inorganic metallic di- or polysulfide compound of the formula $M_2S_n$ containing unbranched $[S_n]^{2-}$ ions, where M designates a metal and n is any number from 2 to the maximum value of n, which polysulfide upon topical administration itself has an objectionable odor, said powder comprising about 10-70% by weight of a montmorillonite clay based on the weight of the total composition and about 2-30% by weight of attapulgite based on the weight of the total composition, said powder being present in an amount to deodorize said composition, to absorb and adsorb the skin oils and to release an effective amount of said polysulfide compound to treat said patient.

11. The composition according to claim 10, wherein said polysulfide compound is in the form of a sulfurated lime solution.

12. The composition according to claim 10, wherein said polysulfide compound is selected from the group consisting of alkali metal and alkaline earth metal polysulfides.

13. The composition according to claim 10, including a pharmaceutically acceptable surfactant and a lower alkanol.

14. The composition according to claim 10, wherein said montmorillonite clay is selected from the group consisting of bentonite, hectorite, smectite, kaolin and saponite.

15. The composition according to claim 10, wherein said composition includes one filler selected from the group consisting of talc and calcium carbonate.

16. The composition according to claim 10 including an effective amount of a compound selected from the group consisting of benzoyl peroxide, erythromycin, retinoic acid, salicylic acid or resorcinol.

17. The composition according to claim 10 includes an antibiotic agent in the amount of about 1-6% by weight of the total composition.

18. The composition according to claim 10, wherein said polysulfide is calcium polysulfide.

* * * * *